United States Patent [19]
Walter et al.

[11] Patent Number: 5,725,382
[45] Date of Patent: Mar. 10, 1998

[54] SELF-CONTAINED, INTERACTIVE TOILET TRAINING KIT FOR CHILDREN AND CAREGIVERS

[75] Inventors: James Andrew Walter; Shirlee Ann Weber; Mark Thomas Cammarota, all of Neenah, Wis.

[73] Assignee: Kimberly-Clark Worldwide, Inc.

[21] Appl. No.: 709,246

[22] Filed: Aug. 30, 1996

[51] Int. Cl.$^6$ ............................................ G09B 19/00
[52] U.S. Cl. ................... 434/258; 434/238; 206/581; 206/459.5
[58] Field of Search ................. 434/84, 238, 258, 434/247, 260; 206/581, 459.5, 494, 440, 570, 803; D3/203, 206, 315; D9/319, 341, 457, 414; D19/59, 62

[56] References Cited

U.S. PATENT DOCUMENTS

| | | | |
|---|---|---|---|
| Re. 26,520 | 1/1969 | Sellars, Jr. et al. | 4/134 |
| D. 256,735 | 9/1980 | Denk | D30/99 |
| D. 258,679 | 3/1981 | Johnson | D23/53 |
| D. 276,361 | 11/1984 | Hyman, Sr. | D23/53 |
| D. 302,583 | 8/1989 | Lemmeyer | D23/296 |
| D. 308,989 | 7/1990 | Cohen | D20/39 |
| D. 310,118 | 8/1990 | Lemon | D23/297 |
| D. 310,869 | 9/1990 | Sedlack | D23/296 |
| D. 311,058 | 10/1990 | Brunel | D23/296 |
| D. 316,278 | 4/1991 | Cohen | D20/39 |
| D. 318,325 | 7/1991 | McKiney | D23/302 |
| D. 320,845 | 10/1991 | Lambdin | D23/297 |
| D. 321,041 | 10/1991 | Lambdin | D23/297 |
| D. 321,045 | 10/1991 | Lambdin | D23/297 |
| D. 321,046 | 10/1991 | Lambdin | D23/297 |
| D. 321,246 | 10/1991 | Lambdin | D23/297 |
| D. 321,247 | 10/1991 | Lambdin | D23/297 |
| D. 324,906 | 3/1992 | Barnett | D23/296 |
| D. 330,225 | 10/1992 | Cohen | D20/42 |
| D. 340,512 | 10/1993 | Geneve et al. | D23/296 |
| D. 341,650 | 11/1993 | Burden | D23/297 |

(List continued on next page.)

FOREIGN PATENT DOCUMENTS

| | | | |
|---|---|---|---|
| 1152255 A | 8/1983 | Canada | A47K 13/06 |
| 2001725 | 5/1990 | Canada . | |
| 1290102 C | 10/1991 | Canada | A47K 11/02 |
| 2040602 A1 | 10/1991 | Canada | A61F 13/15 |
| 2049213 A1 | 6/1992 | Canada | A63H 3/20 |
| 2098891 A1 | 12/1994 | Canada | A47K 11/12 |
| 2137849 A1 | 5/1996 | Canada | A47K 10/16 |
| 0313689 | 5/1989 | European Pat. Off. | 206/581 |
| 2690136 | 10/1993 | France . | |
| WO 90/03156 A1 | 4/1990 | WIPO | A61F 13/15 |
| WO 90/11714 A1 | 10/1990 | WIPO | A47K 11/06 |
| WO 91/17730 A1 | 11/1991 | WIPO | A61F 5/48 |
| WO 95/05774 A1 | 3/1995 | WIPO | A61B 5/20 |
| WO 95/24853 A1 | 9/1995 | WIPO | A47K 11/02 |
| WO 96/19168 A2 | 6/1996 | WIPO | A61F 13/15 |
| WO 96/19172 A1 | 6/1996 | WIPO | A61F 13/42 |

OTHER PUBLICATIONS

Golden Books Toilet Training Kit Photographs (2).
Uni–Charm Toilet Training Kit Photographs (7).
Star Kids Products Toilet Training Kit Photographs (5).
Barron's Toilet Training Kit Photographs (7).
Positive Action Learning Systems, Inc. Toilet Training Kit Photographs (2).

*Primary Examiner*—Jeffrey A. Smith
*Attorney, Agent, or Firm*—Douglas L. Miller

[57] ABSTRACT

A child's self-contained, interactive toilet training kit made from a relatively rigid material and having a lid that is moveable between an open position and a closed position. The kit includes a plurality of training pants, a plurality of interactivity devices adapted for use by a caregiver for instructing a child in toilet training, and a plurality of activity devices adapted for use by the child for encouraging the child in toilet training.

11 Claims, 7 Drawing Sheets

U.S. PATENT DOCUMENTS

| | | | |
|---|---|---|---|
| D. 341,853 | 11/1993 | Cohen | D20/42 |
| D. 343,891 | 2/1994 | Kessler | D23/297 |
| D. 345,202 | 3/1994 | Crossley et al. | D23/296 |
| D. 350,819 | 9/1994 | Laroue | D23/296 |
| D. 351,223 | 10/1994 | Wise et al. | D23/296 |
| D. 351,224 | 10/1994 | Wise et al. | D23/296 |
| D. 352,993 | 11/1994 | Boucher et al. | D23/297 |
| D. 354,342 | 1/1995 | Marshall-Smith | D23/309 |
| D. 356,633 | 3/1995 | Nunn | D23/297 |
| D. 363,343 | 10/1995 | Azimi-Bolourian | D23/309 |
| D. 366,931 | 2/1996 | Blackburn | D23/309 |
| D. 369,856 | 5/1996 | Lucido et al. | D23/310 |
| D. 377,452 | 1/1997 | Boone | D10/40 |
| 2,512,485 | 6/1950 | Cougias | 434/238 |
| 2,644,259 | 7/1953 | Beadle | 206/459.5 X |
| 2,825,208 | 3/1958 | Anderson | 206/581 X |
| 2,874,707 | 2/1959 | Koppel | 206/581 X |
| 3,172,390 | 3/1965 | Garthofner | 116/67 |
| 3,176,319 | 4/1965 | Mackey | 43/134 |
| 3,205,509 | 9/1965 | Rose | 4/107 |
| 3,251,072 | 5/1966 | Breed | 4/239 |
| 3,343,179 | 9/1967 | Sellars, Jr. et al. | 4/134 |
| 3,364,478 | 1/1968 | Waard | 340/272 |
| 3,400,874 | 9/1968 | Shimada et al. | 229/11 |
| 3,416,163 | 12/1968 | Jordan | 4/134 |
| 3,428,967 | 2/1969 | Hughes | 4/142 |
| 3,495,277 | 2/1970 | Herskovich | 4/134 |
| 3,583,093 | 6/1971 | Glass et al. | 46/117 |
| 3,592,195 | 7/1971 | Van Wagenen et al. | 128/295 |
| 3,688,742 | 9/1972 | McGee | 119/1 |
| 3,691,980 | 9/1972 | Shastal | 116/67 |
| 3,747,834 | 7/1973 | Schillinger | 229/20 |
| 4,044,405 | 8/1977 | Kreiss | 4/1 |
| 4,162,490 | 7/1979 | Fu et al. | 340/603 |
| 4,205,404 | 6/1980 | Levins | 4/254 |
| 4,285,156 | 8/1981 | Leistikow et al. | 46/14 |
| 4,373,715 | 2/1983 | Henn | 272/1 R |
| 4,381,568 | 5/1983 | Brown | 4/239 |
| 4,413,441 | 11/1983 | Hunter et al. | 46/116 |
| 4,437,430 | 3/1984 | DeBardeleben | 119/1 |
| 4,443,200 | 4/1984 | Murphy | 434/247 |
| 4,503,571 | 3/1985 | Sidney | 4/254 |
| 4,504,241 | 3/1985 | Dyson et al. | 446/304 |
| 4,509,215 | 4/1985 | Paz | 4/452 |
| 4,516,279 | 5/1985 | Block | 4/235 |
| 4,534,463 | 8/1985 | Bouchard | 206/267 |
| 4,560,359 | 12/1985 | Wilson et al. | 434/84 X |
| 4,565,335 | 1/1986 | Rankin | 242/55.2 |
| 4,633,536 | 1/1987 | Tribble-DuBose | 4/460 |
| 4,685,559 | 8/1987 | Titus . | |
| 4,702,378 | 10/1987 | Finkel et al. | 206/581 |
| 4,706,845 | 11/1987 | Schnurer et al. | 221/102 |
| 4,744,113 | 5/1988 | Kogut | 4/661 |
| 4,759,086 | 7/1988 | Booth-Cox | 4/451 |
| 4,773,863 | 9/1988 | Douglas, III | 434/247 |
| 4,776,800 | 10/1988 | Anderson | 434/247 |
| 4,777,672 | 10/1988 | Gebhard et al. | 4/449 |
| 4,777,680 | 10/1988 | Paz | 4/484 |
| 4,805,765 | 2/1989 | Barrett et al. | 206/45.1 |
| 4,820,164 | 4/1989 | Kemper | 434/238 |
| 4,848,588 | 7/1989 | Rasmussen | 206/581 |
| 4,882,794 | 11/1989 | Stewart, III | 4/451 |
| 4,883,749 | 11/1989 | Roberts et al. | 434/247 |
| 4,909,804 | 3/1990 | Douglas, Sr. | 604/385.2 |
| 4,944,733 | 7/1990 | Casale | 604/385.1 |
| 5,005,224 | 4/1991 | Carmichael | 4/300.3 |
| 5,008,964 | 4/1991 | Dean et al. | 4/661 |
| 5,031,253 | 7/1991 | Brendlinger | 4/300.3 |
| 5,038,703 | 8/1991 | Frush | 116/170 |
| 5,040,248 | 8/1991 | Kelly | 4/462 |
| 5,044,020 | 9/1991 | Lewandowski et al. | 4/301 |
| 5,048,463 | 9/1991 | Wilson et al. | 119/163 |
| 5,074,317 | 12/1991 | Bondell et al. | 128/886 |
| 5,077,840 | 1/1992 | Masters et al. | 4/300.3 |
| 5,083,325 | 1/1992 | Vitullo | 4/479 |
| 5,094,644 | 3/1992 | Kelley | 446/305 |
| 5,103,772 | 4/1992 | Schmid | 119/162 |
| 5,107,985 | 4/1992 | Bezrutczyk et al. | 206/45.15 |
| 5,117,515 | 6/1992 | White, Jr. et al. | 4/661 |
| 5,117,780 | 6/1992 | Wooten et al. | 119/162 |
| 5,123,130 | 6/1992 | Sanders | 4/661 |
| 5,155,871 | 10/1992 | Sams | 4/484 |
| 5,161,263 | 11/1992 | Geneve et al. | 4/483 |
| 5,246,161 | 9/1993 | Kapp | 206/459.5 X |
| 5,252,101 | 10/1993 | Rosenwinkel et al. | 446/130 |
| 5,276,595 | 1/1994 | Patrie | 362/101 |
| 5,282,283 | 2/1994 | Atkin | 4/661 |
| 5,285,540 | 2/1994 | Putz | 4/661 |
| 5,309,580 | 5/1994 | Amalsad et al. | 4/483 |
| 5,343,577 | 9/1994 | Petrovich | 4/661 |
| 5,353,449 | 10/1994 | Rubenstein et al. | 4/661 |
| 5,355,837 | 10/1994 | Reyes | 119/161 |
| 5,363,516 | 11/1994 | Butts | 4/661 |
| 5,365,496 | 11/1994 | Tolan-Samilow | 368/109 |
| 5,369,820 | 12/1994 | Blount | 4/483 |
| 5,415,475 | 5/1995 | Sandy | 383/8 |
| 5,416,469 | 5/1995 | Colling | 340/573 |
| 5,429,373 | 7/1995 | Chelko et al. | 273/440 |
| 5,432,956 | 7/1995 | Park | 4/239 |
| 5,435,459 | 7/1995 | Huck et al. | 221/70 |
| 5,443,161 | 8/1995 | Jonese | 206/581 |
| 5,458,089 | 10/1995 | Rymer | 119/162 |
| 5,465,431 | 11/1995 | Wertz | 4/300.3 |
| 5,509,149 | 4/1996 | Lynch | 4/476 |
| 5,509,808 | 4/1996 | Bell | 434/247 |
| 5,513,396 | 5/1996 | Tsipov | 4/420 |
| 5,518,405 | 5/1996 | Aiello | 434/258 |
| 5,535,456 | 7/1996 | Chai | 4/449 |
| 5,537,695 | 7/1996 | Ander | 4/483 |
| 5,560,051 | 10/1996 | Butts | 4/479 |
| 5,568,128 | 10/1996 | Nair | 340/604 |
| 5,573,407 | 11/1996 | Dunford | 434/262 |
| 5,575,021 | 11/1996 | Harris | 4/449 |

SELF-CONTAINED, INTERACTIVE TOILET TRAINING KIT FOR CHILDREN AND CAREGIVERS

BACKGROUND OF THE INVENTION

The present invention relates to toilet training for children, and particularly to a self-contained, interactive toilet training kit useful both to a child and a caregiver for instructing and encouraging the child in the toilet training process.

From birth to an age of about two years old, a little boy or girl wears diapers until he or she is ready for the toilet training process, when they learn to use the toilet by themselves. Some children may start the toilet training process as early as the age of fifteen months, while others may not be ready until after the age of two years. The age at which a child will begin this training process is dependent upon many factors, some of which are psychological, some physiological, and some unique to the individual child or their environment.

The toilet training process embraces a number of aspects, some of which may or may not apply to each child. One aspect of the total toilet training process is the change from diapers to training pants to help the child understand that he or she should now use the toilet just like grownups.

Another aspect of the total toilet training process includes parental or caregiver instruction as a positive encouragement and reinforcement to the child that he or she should now be using a toilet, instead of diapers. Although the use of training pants and positive encouragement from the parent or caregiver has been helpful in the toilet training process, there is still much room for improvement. Specifically, parents and caregivers are still searching for an easier and quicker way for guiding their children successfully through the toilet training process.

Many caregivers, such as parents, have difficulty in determining the readiness of a child to begin the toilet training process, and underestimate the difficulty of teaching the toilet training process to young children. If a child does not respond to an initial toilet training instruction or introduction, the caregiver can be at a loss for finding techniques, methods, or teaching tools to encourage the child to master the art of toilet training.

Currently, various teaching tools are available and include books, videotapes, charts with stickers, personalized toilets, packages that include a boy or girl doll and a toilet for the doll, along with one or more of the previously mentioned items. However, none of these products have solved the need for a method or technique for making the toilet training process easier and quicker, both for the caregiver and the child.

SUMMARY OF THE INVENTION

In response to the discussed difficulties and problems encountered in the prior art, a self-contained, interactive toilet training kit has been discovered.

In one form of the present invention, there is provided a self-contained, interactive toilet training kit including a case having a bottom wall, a continuous side wall forming with the bottom wall an interior and an opening, and a lid that is moveable between a closed position that covers the opening and an open position that exposes the opening. The kit further includes an interactivity device for instructing the child in the toilet training process, and an activity device for use by the child for encouraging the child during the toilet training process.

In still another form of the present invention, there is provided a self-contained, interactive toilet training kit including a case having an interior and including a bottom wall, a continuous side wall, and a lid moveable between a closed position and an open position. At least one partition is in the interior that divides the interior into at least two compartments. A plurality of training pants are in one of the compartments, and at least one activity device in another compartment. An interactivity device also is included for instructing a child in toilet training.

BRIEF DESCRIPTION OF THE DRAWINGS

The above-mentioned and other features of the present invention and manner of attaining them will become more apparent, and the invention itself will be better understood by reference to the following description of the invention, taken in conjunction with the accompanying drawings wherein.

DETAILED DESCRIPTION

Figure 1:
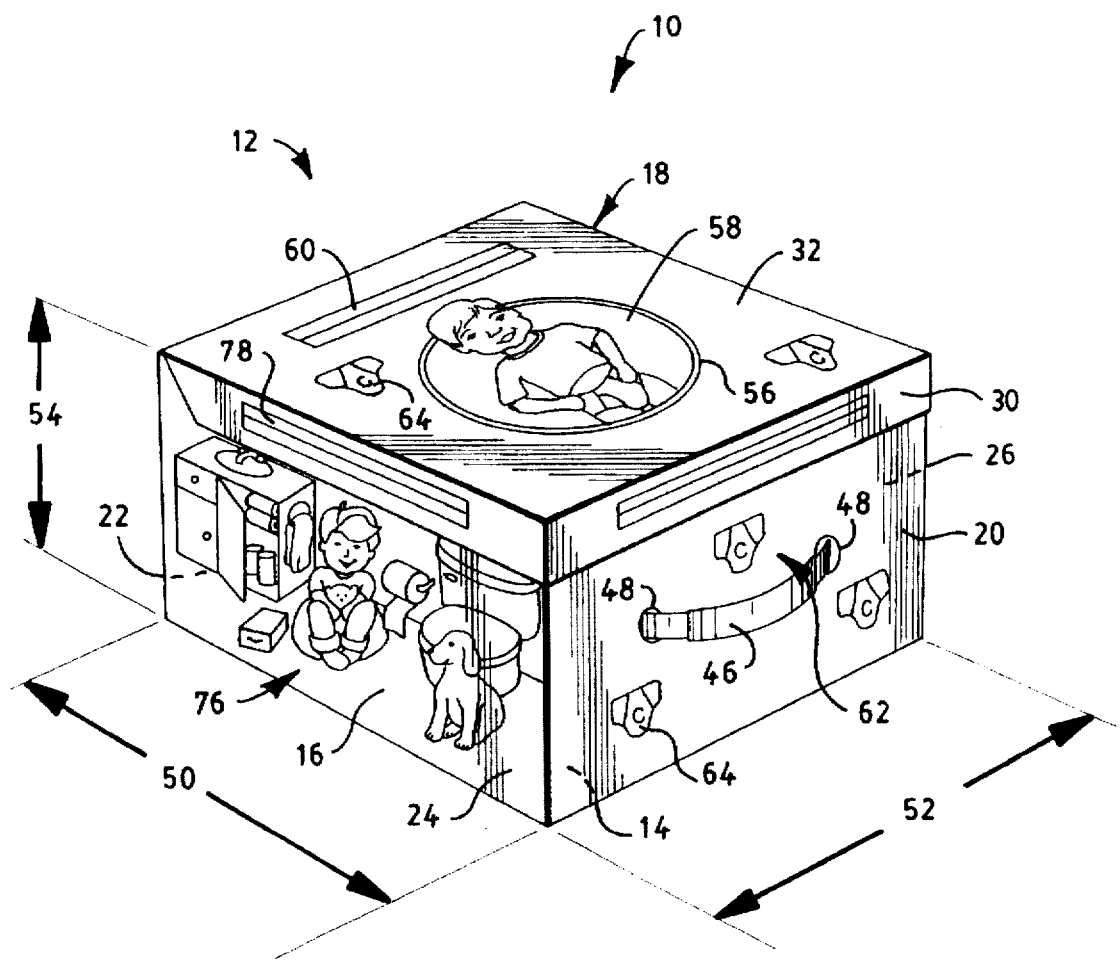
FIG. 1 illustrates a perspective view of one embodiment of the present invention.

One of the most important desires of caregivers in the toilet training process is that the process should be easier and quicker, both for the caregivers as well as the child. The term "caregiver" refers to parents, babysitters, friends, teachers, or the like. However, for purposes of style only, the term "mother" or "mothers" will be used, in conjunction with her child, in describing the invention hereafter. The toilet training process is not a simple and easy step-by-step procedure resulting in immediate success, but rather usually involves an extended time-consuming effort by a mother and her child, which often is beset with many frustrations and problems. With the advent of the disposable absorbent training pant, it was thought that the toilet training process would be a much simpler process for the child. However, it has been discovered that the toilet training process continues to be a complicated exercise and challenging experience for both the child and mother. For example, many of the problems involved in the toilet training process are due to physiological factors; psychological factors, both for the child and the mother; the many different approaches to toilet training practiced by mothers; inconsistent application of a toilet training process; or the like. Because of this, other areas and practices, apart from training pant-related ones, were investigated with the view of making the toilet training process easier and quicker.

The result of these efforts is the discovery of a self-contained, interactive toilet training kit for use by children and mothers. In studying the toilet training process, it was discovered that children can progress more easily through the toilet training process if given educational and motivational activities uniquely designed for their age and experience level. The toilet training kit was discovered to be a highly motivational and educational instrument for use both by the child and the mother. Specifically, the kit provides positive and encouraging interaction between the mother and the child. For example, this interaction is initiated when the mother presents the kit to the child and begins to explain its use. Thus, the kit creates a positive, cooperative atmosphere between the mother and child eventually resulting in the child wanting to toilet train. Motivating the child to want to toilet train is a crucial factor in learning and successfully completing the toilet training process.

Also, it can be difficult for a mother to know when her child is interested in and ready to toilet train. Currently, about half the children entering the toilet training process in the United States are their mothers' first child, so these mothers often are inexperienced in teaching this skill. Uniquely, the toilet training kit can be used by the mother for determining the readiness and interest of her child in the toilet training process, and then in preparing the child for that training. Examples of readiness are the ability to follow directions, to understand words involved with toilet training, to show an interest in the toilet, or the like. The kit can be used to prepare the child for toilet training, to reinforce positive behavior, and to encourage independence, so that the child will master the art of toilet training.

Also, children at this age begin to become independent in some of their activities. This independence can manifest itself with a certain degree of obstinateness. Unsurprisingly, this obstinate behavior can be antithetical to any instruction from the mother or to a process intended to encourage and motivate a child successfully through the toilet training process. In another unique aspect of the present invention, the toilet training kit provides a motivation to toilet train that is separate from and supplements the mother's efforts by giving the child a sense of ownership not only in the kit, but also in his or her successful completion of toilet training.

The toilet training kit of the present invention thus complements a mother's plan or method in toilet training her child by, among other things, making the child feel unique and special, and giving the child the motivation to progress through the toilet training process.

Figure 2:
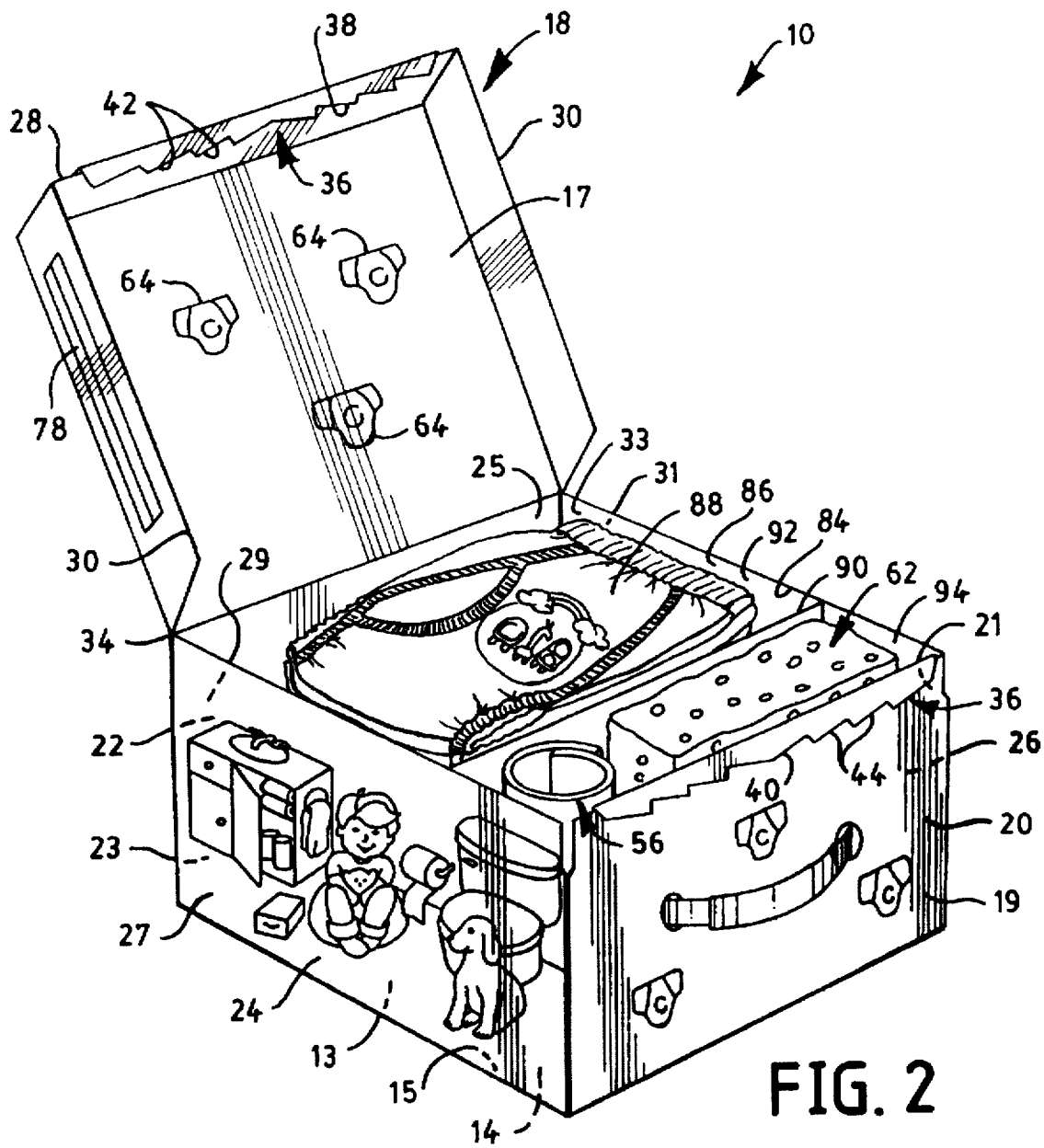
FIG. 2 illustrates the embodiment in FIG. 1 with the lid in an open position.

Referring now primarily to FIGS. 1 and 2, there is illustrated a child's toilet training kit 10 of the present invention. The kit can be designed to be either reusable or disposable. The term "reusable" means that once the contents of kit 10 have been depleted, the kit 10 can be replenished with new contents. The term "disposable" means that once the original contents of the kit 10 have been depleted, the kit 10 can then be properly disposed of. The kit 10 is self-contained and portable in that it holds all of the desired devices, and is easily carried and used by the child in the toilet training age range. The portability feature is also important for providing the sense of ownership earlier described above.

Kit 10 comprises a case 12 including a bottom wall 14, a continuous side wall 16, and a moveable lid 18. As illustrated in FIG. 1, case 12 has a hexahedral shape, in that it has six planar, i.e., flat, surfaces. Bottom wall 14 and lid 18 comprise two of the planar surfaces, while continuous side wall 16 includes a front wall 20, a back wall 22, a left wall 24 as viewed looking directly at front wall 20, and a right wall 26. Referring to FIG. 2, bottom wall 14 includes an outer surface 13 and an inner surface 15, lid 18 includes an inner surface 17 and a top surface 32 (FIG. 1), front wall 20 includes an outer surface 19 and an inner surface 21, back wall 22 includes an outer surface 23 and an inner surface 25, left wall 24 includes an outer surface 27 and an inner surface 29, and right wall 26 includes an outer surface 31 and an inner surface 33. The case 12 desirably has this hexahedral shape so that it can be designed to resemble a toy carrying case or a doll case. Other interesting and fun designs for a child include a lunchbox, a back pack, a gym bag, or the like. The attractive design serves to further interest and motivate the child to toilet train.

As mentioned above, the present invention contemplates case 12 having other designs or shapes. For example, continuous side wall 16 can comprise three planar walls, rather than the four planar walls described above. Furthermore, continuous side wall 16 can have an arcuate shape, for example, circular, oval, or the like. The arcuate shape can give case 12 the appearance of a hat box or a similar case that would be suitable or desirable to a child.

As illustrated in FIG. 1, lid 18 is in a closed position, but is moveable to an open position illustrated in FIG. 2. With reference to FIG. 2, lid 18 includes a top surface 32 (FIG. 1), a front flange 28 that extends downwardly, as viewed in FIG. 1, from top surface 32, and a pair of side flanges 30 that similarly extend downwardly. Flanges 28, 30 overlap portions of front wall 20 (FIG. 1) and left and right walls 24, 26, respectively. Lid 18 can be a structure separate from the remaining portion of case 12, or can be connected to case 12 by, for example, a hinge 34 at back wall 22. Hinge 34 can be provided in any suitable manner well known in the art, and one such manner is accomplished by forming case 12 from a single layer of material that is suitably cut and folded into a hexahedral shape. In this manner, hinge 34 is one of the fold lines provided in the layer of material. Optionally, case 12 can be manufactured or constructed from separate layers of material that are suitably joined or adhered together to form the desired shape. Thus, the term "continuous side wall" is not limited to mean formed of one integral piece or layer.

As previously described, kit 10 is desirably intended to be reusable, and accordingly it is desirable that case 12, as well as its contents and other fixtures, be made of a relatively durable material. Examples of such durable materials include corrugated cardboard, paperboard, wood, synthetic materials treated to be stiff or rigid, or the like. One such suitable case 12 is commercially available from the Waldorf Corporation of Chicago, Ill. This case is identified as design number 6068; style: seal end with handle; board: 0.022SBS.

In order to maintain lid 18 in the closed position, as illustrated in FIG. 1, a locking means or device 36 (FIG. 2) is provided and comprises a serrated flange or flap 38 on lid 18, and a serrated flange or flap 40 on continuous side wall 16. As illustrated in FIG. 2, lid serrated flange 38 is provided on front flange 28 and disposed inwardly thereof, while wall serrated flange 40 is disposed along and inwardly of front wall 20. When in the closed position (FIG. 1), the teeth 42 of lid serrated flange 38 releasably interlock or releasably engage the teeth 44 of wall serrated flange 40. The serrated flanges 38, 40 can be a part of a single layer of material that is die cut and folded in order to form the shape of case 12, or can be separate structure joined in any suitable manner to lid 18 and front wall 20. If desired, the serrated flange 38 can also be provided along side flanges 30, and serrated flange 40 may also be provided along left and right walls 24, 26 in order to provide additional security to lid 18 in the closed position. Furthermore, if the design and construction of case 12 is such that lid 18 is a separate structure from the remaining portion of case 12, then the serrated flange 38 can be provided along the complete peripheral portion of lid 18, as well as providing serrated flange 40 along the complete peripheral portion of continuous side wall 16.

In order to provide ease of portability and use to the child, a carrying handle 46 (FIG. 1) is provided in front wall 20. In the embodiment illustrated in FIG. 1, front wall 20 has a pair of holes 48 that receive the ends of carrying handle 46, with the ends (not illustrated) of carrying handle 46 having a larger dimension than the diameter of holes 48 in order to secure handle 46 to front wall 20. Carrying handle 46 can be made of any suitably durable material, such as plastic, rope, cardboard, fabric, or the like, and its design should allow the child to use it easily and repeatedly.

Ease of portability for the child is important since this permits the child to easily use the kit 10, thus giving the child a sense of ownership. This is part of the positive encouragement and motivation provided by the present invention throughout the toilet training process. Desirably, case 12 has a length dimension 50 (FIG. 1) no greater than about 16 inches and desirably about 8 inches, a width dimension 52 no greater than about 16 inches and desirably about 9 inches, and a height dimension 54 no greater than about 16 inches and desirably about 5½ inches. If the case 12 is much larger than this, kit 10 may be too difficult for the child to carry and use.

Earlier, mention was made of interaction between the mother and the child as a means of encouraging and motivating the child to begin and successfully progress through the toilet training process. In order to promote that interaction, the present invention provides an interactivity means or device to be used by the mother and child for instructing and aiding in toilet training. Typical examples of interactivity means or devices include, but are not limited to, a two-dimensional learning graphic illustrating a child using the toilet properly, a two-dimensional learning graphic illustrating a child pulling up or pulling down a training pant properly; educational materials; informational materials; flash cards; reward items; videotapes; or the like. These examples are typical of an interactivity means or device that creates the appropriate interaction between a mother and a child. For example, a graphic illustrating a child using the toilet properly can be used by the mother to explain to her child how he or she can use the toilet in the same manner. Similarly, other two-dimensional learning graphics, flash cards, stickers and an associated progress chart, educational or informational materials, or the like can be used by the mother to encourage and motivate her child in toilet training. These interactivity devices can be linked or associated together with common graphics or characters to reinforce the learning process in toilet training. This positive interaction between the mother and the child, which creates an encouraging and motivational atmosphere for the child, is extremely important in the child's progressing through the toilet training process easily and quickly.

Another feature of the present invention, in addition to the interactivity means or devices described above, are activity devices or means to be used by the child in toilet training. These activity devices or means are intended to be used independently by the child to encourage and motivate the child through the toilet training process. For example, the activity devices or means can acquaint and educate the child to toilet training, provide the motivation for the child to desire to toilet train, create a sense of ownership and independence in the child that encourages the child to progress through toilet training, or the like. Examples of these activity devices or means include, but are not limited to, crayons, a graphic to be colored, colored pre-printed graphics, urine targets, or the like.

In the description hereafter, toilet training kit 10 will be described as having specific interactivity devices or activity devices on various walls and surfaces thereof, but it should be recognized that any combination of the placement of interactivity devices and activity devices on the walls and their surfaces can be used in accordance with the present invention. The numerous combinations and variations of these devices illustrate the flexibility of the present invention in toilet training, and can be used to attract the attention of the child to the kit 10 as a first step in the toilet training process.

Figure 3:
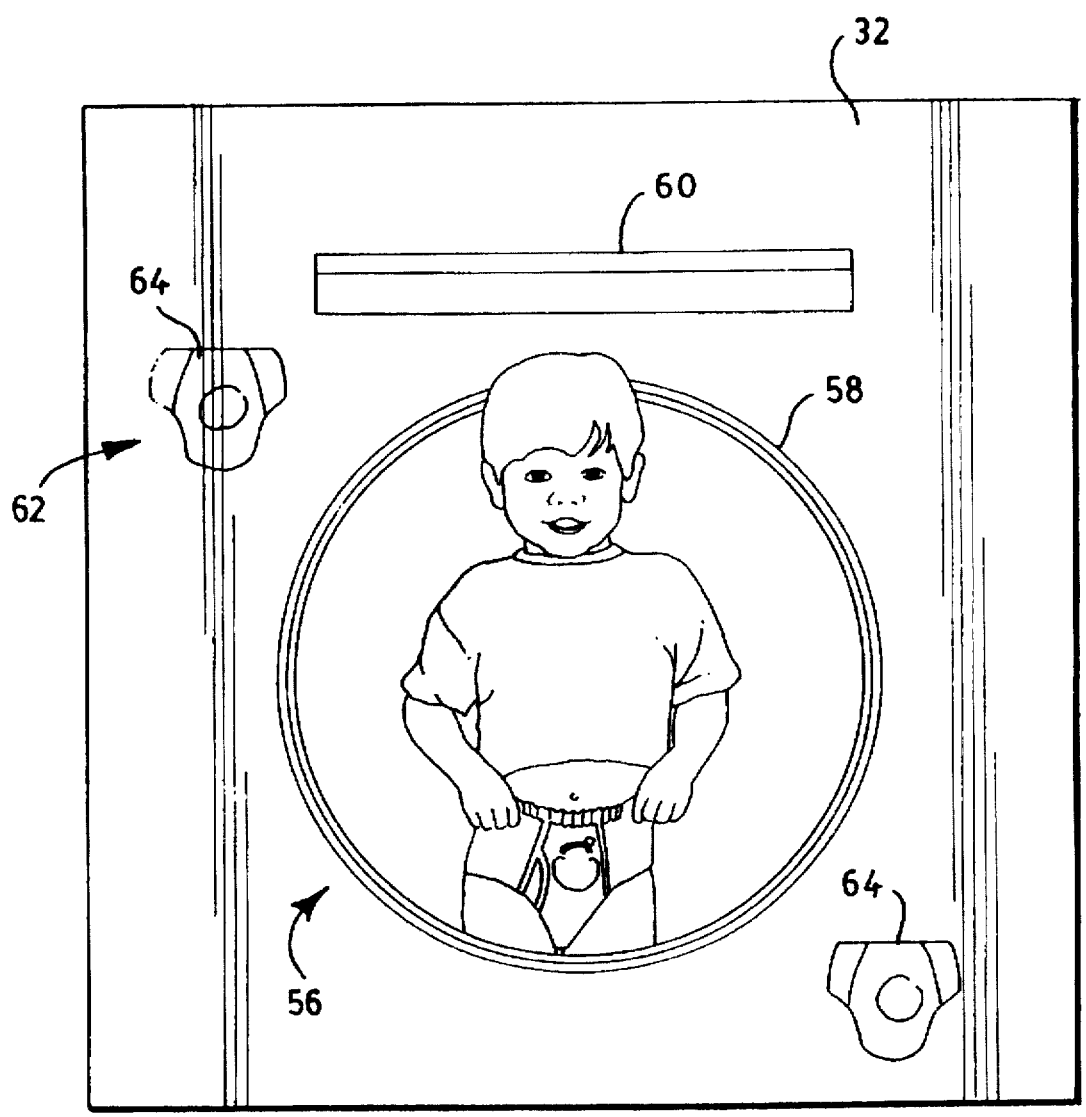
FIG. 3 illustrates a top plan view of the embodiment in FIG. 1.

With reference now to FIGS. 1 and 3, top surface 32 of lid 18 has an interactivity means or device 56 that includes a pre-printed, colored graphic 58 of a child pulling a training pant upwardly to the waist. This particular interactivity device 56 can be used by the mother to properly instruct and encourage the child in the proper position or fit of the training pant. Interactivity device 56 further includes educational information 60, which can be used in conjunction with graphic 58 to assist the mother in properly instructing and encouraging the child. Optionally, this, another activity device 56, or an interactivity device 62 can be provided on inner surface 17 of lid 18 such as, by way of example, training pants 64.

Top surface 32 can also include an activity device or means 62 intended to be used by the child. In this embodiment, activity device 62 is a plurality of training pants 64 provided in a manner to be colored by the child. The activity device 62 gives the child an opportunity to personally use kit 10 in order to provide a sense of ownership, responsibility, and independence in the toilet training process.

Figure 4:
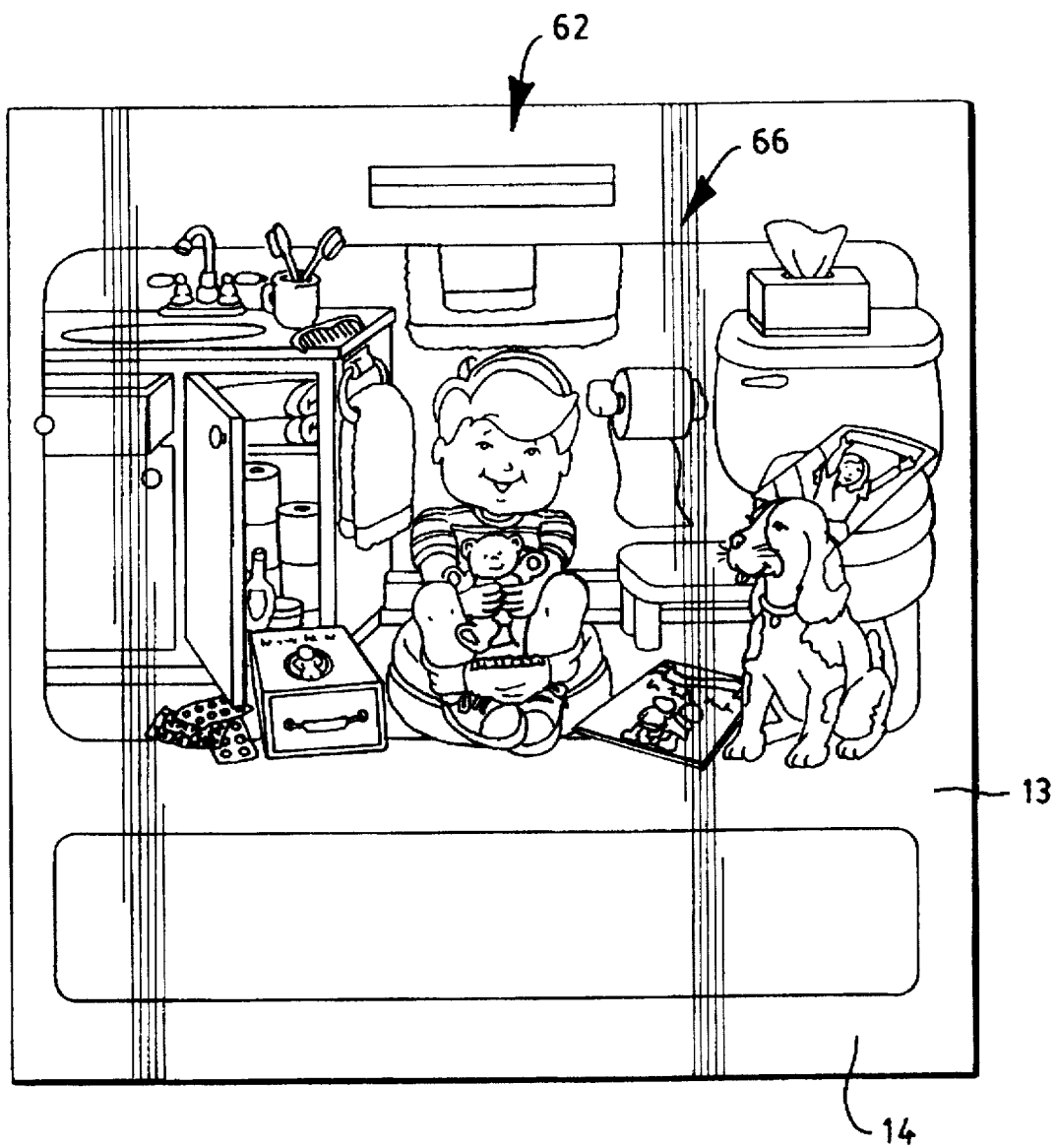
FIG. 4 illustrates a bottom plan view of the embodiment in FIG. 1.

Referring now to FIG. 4, bottom wall 14 includes an activity device 62 on outer surface 13, which in this embodiment is a scene 66 intended to be colored by the child. The scene 66 is instructional in that it illustrates a child in a typical bathroom environment and sitting on the toilet as part of the toilet training process. Naturally, other types of scenes 66 can be provided which are instructional, educational, and motivational to the child. Again, if desired, this or another device 56, 62 can be provided on inner surface 15 (FIG. 2)

Figure 5:
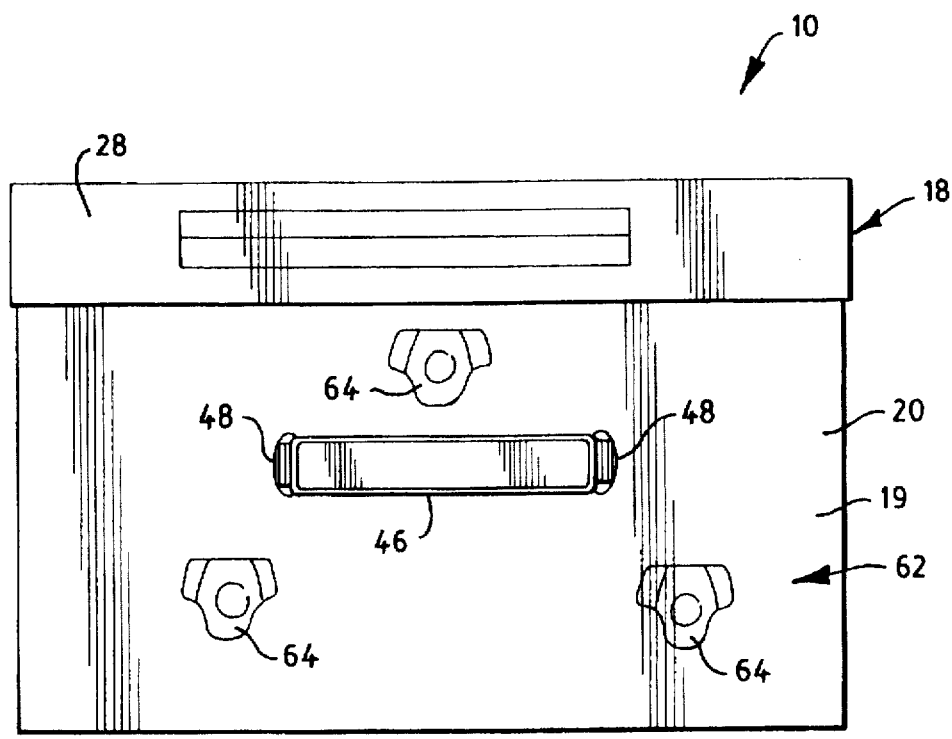
FIG. 5 illustrates a front elevational view of the embodiment in FIG. 1.

Referring now to FIG. 5, front wall 20 of kit 10 also includes training pants 64 on outer surface 19 to be colored by the child. Designs other than training pants 64 can be used, such as toilets, potty chairs, or the like. Although front flange 28 does not include an interactivity device 56 or an activity device 62, it can, of course, have either or both of those provided as desired. Inner surface 21 (FIG. 2) can include other devices 56, 62.

Figure 6:
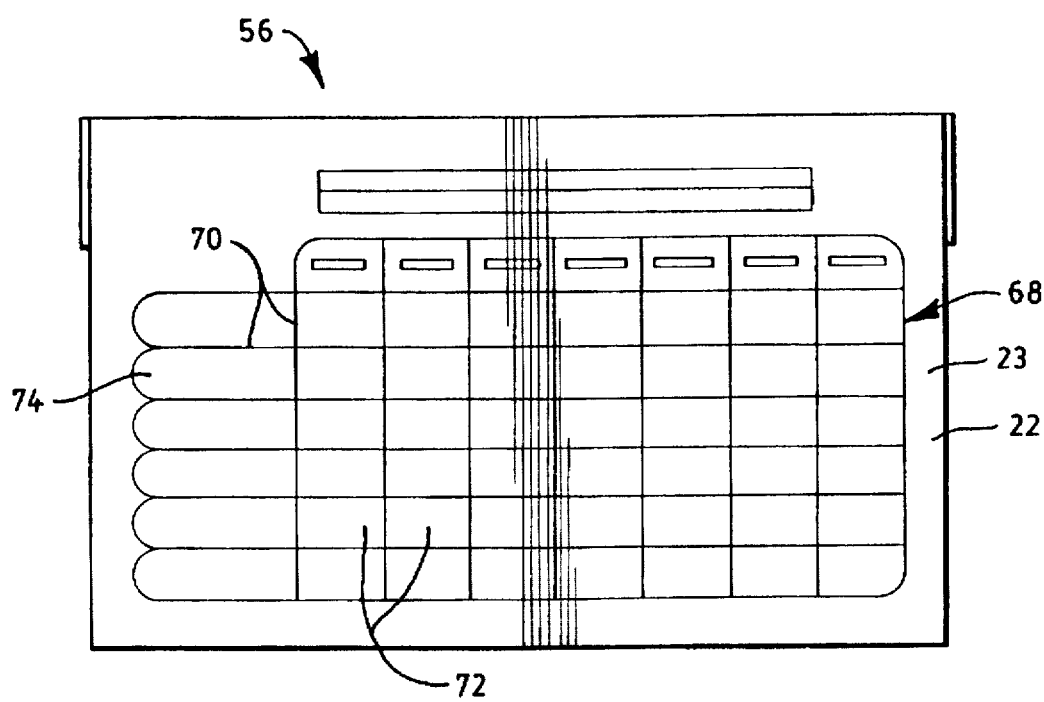
FIG. 6 illustrates a back elevational view of the embodiment in FIG. 1.

With reference to FIG. 6, back wall 22 includes an interactivity device 56 on outer surface 23 in the form of a progress chart 68 comprising intersecting lines 70 that form a plurality of spaces 72. Chart 68 can be used by the mother to encourage, motivate, and monitor the progress of the child during the toilet training process. For example, the mother can write in a first column 74 of spaces 72 different types of rewards or recognitions that the child can receive when successfully going to the toilet. The remaining spaces can identify the days of the week in which the child successfully goes to the toilet, or can be numbered to indicate the number of times the child has successfully gone to the toilet. First column 74 could also identify various steps in the toilet training process, such as properly pulling the training pant up to the correct position at the waist, successfully going to the toilet, successfully using bathroom tissue, or the like, while the uppermost row of spaces can identify various rewards for accomplishing each of the steps in the toilet training process. Thus, chart 68 provides a positive interaction between the mother and the child in order to properly motivate and instruct the child in the toilet training process. Again, other devices 56, 62 can be provided on inner surface 25 (FIG. 2).

Figure 7:
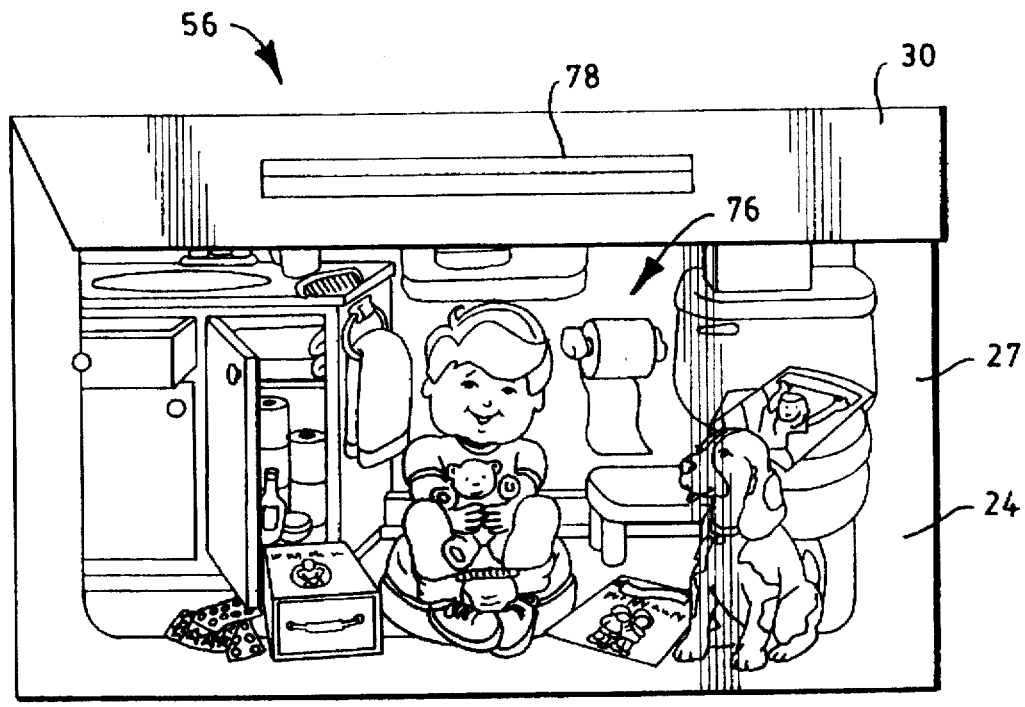
FIG. 7 illustrates a side elevational view of the embodiment in FIG. 1.

Referring now to FIG. 7, left wall 24 includes an interactivity device 56 on outer surface 27 having a scene 76. In this embodiment, scene 76 is a preprinted, colored scene that is designed to give the mother another and different opportunity to instruct and encourage her child. In addition to scene 76, the side flange 30 of lid 18 includes educational information 78 to be used by the mother in explaining scene 76. If desired, inner surface 29 (FIG. 2) can also include other devices 56, 62.

Figure 8:
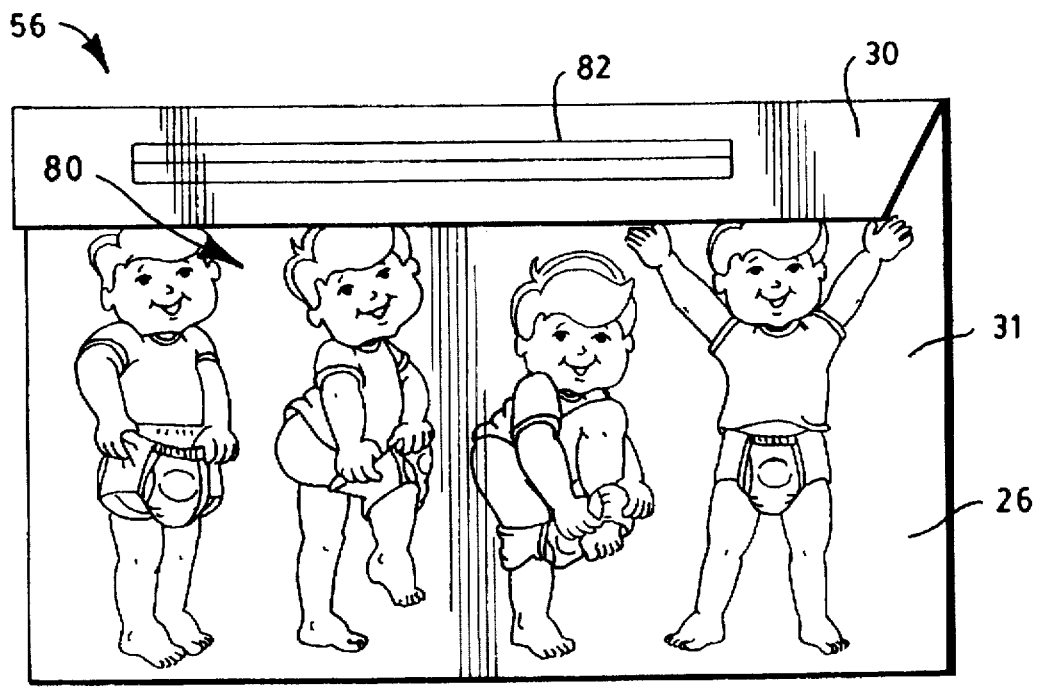
FIG. 8 illustrates an elevational view of the opposite side of the embodiment in FIG. 1.

FIG. 8 illustrates another interactivity device 56 on outer surface 31 that includes a scene 80 illustrating a child properly putting on a training pant, along with educational information 82 assisting the mother in properly explaining to the child the correct way of putting the training pant on. Again, if desired, inner surface 33 (FIG. 2) can also include other devices 56, 62.

With reference to FIG. 2, when lid 18 is in the open position, an opening 84 provides access to the interior 86 of kit 10. The interior 86 can contain those items desirable in assisting the mother in teaching her child proper toilet training habits. The interior 86 can, by way of example, include one or more disposable absorbent training pants 88. In addition, interior 86 can include a partition 90 that separates interior 86 into two compartments, compartment 92 and compartment 94. Compartment 92 can contain the one or more training pants 88, while compartment 94 can contain other items, such as an interactivity device 56, which can be educational information, rolled-up posters for placement at key areas such as the bathroom, and an activity device 62 such as a bag containing small toys, candy, or the like.

Figure 9:
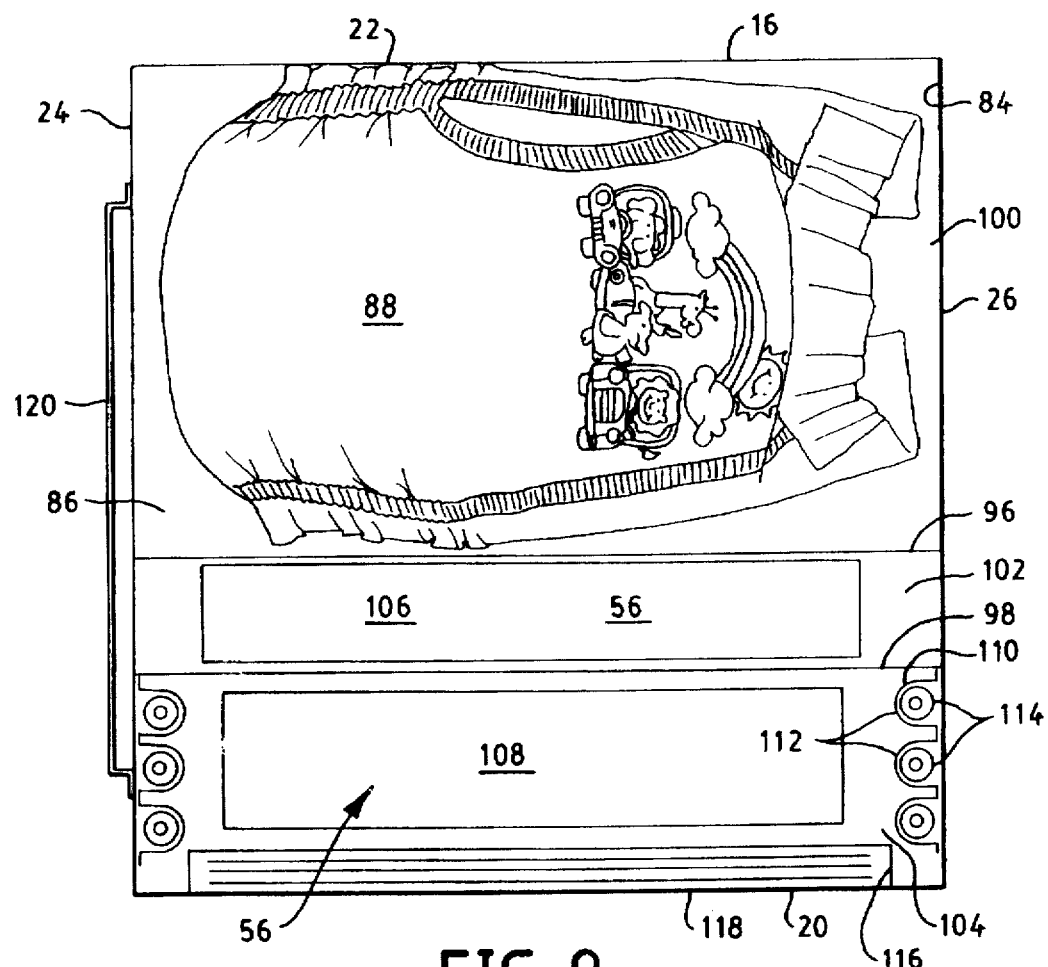
FIG. 9 illustrates a top plan view of the interior of another embodiment of the present invention.

With reference to FIG. 9, interior 86 has a different design and arrangement from that in FIG. 2. In FIG. 9, a series of partitions divides interior 86 into a plurality of compartments for containing various items. Partitions 96, 98 divide interior 86 into three major compartments 100, 102, and 104. These compartments 100, 102, 104 are generally rectangular in shape, but the present invention contemplates other partitions dividing the interior 86 into any number of compartments having any number of desired shapes. Compartment 100 contains the one or more training pants 88 for use by the child. Compartment 102 includes an interactivity device 56 such as a video cassette 106. The video cassette 106 can be shown to the child by the mother and may include an audio-visual presentation on toilet training, personal hygiene, or the like. Compartment 104 is illustrated as containing several items. One of these items is an interactivity device 56 such as educational information 108. Compartment 104 further includes several additional partitions dividing compartment 104 into other smaller compartments. For example, compartment 104 includes two semi-cylindrically shaped partitions 110 forming elongate compartments 112 for containing, by way of example, crayons 114. Crayons 114 can be used to color the appropriate scenes provided on case 12. Another partition 116 within compartment 104 forms an interior pocket 118 that can be used to contain items such as stickers to be used with a progress chart, such as chart 68 (FIG. 6), or the like. Finally, an exterior pocket 120 can be constructed on any of the walls of case 12, such as by way of example, left wall 24. Exterior pocket 120 can be formed of the single layer of material of which case 12 is formed, or can be a separate structure suitably joined to left wall 24. The exterior pocket 120 can be empty to give the child storage capacity for his or her use, or can contain other toilet training items such as stickers, flash cards, or the like.

Figure 10:
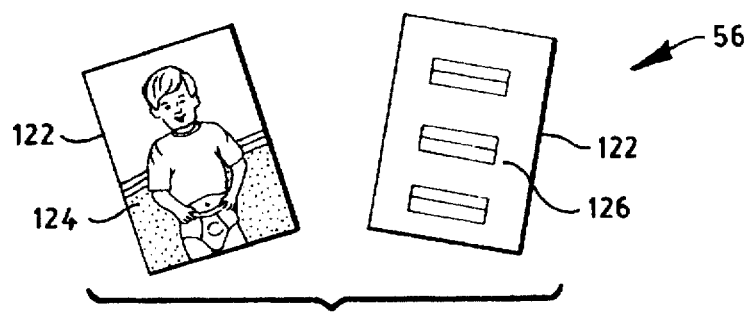
FIG. 10 illustrates one type of interactivity device.
Figure 11:
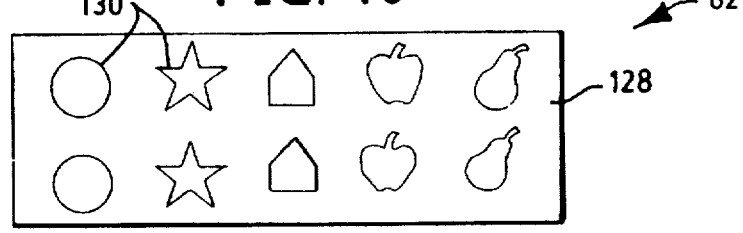
FIG. 11 illustrates one type of an activity device.

FIGS. 10 and 11 illustrate the types of devices 56, 62 that can be used with toilet training kit 10. In FIG. 10, a single flash card 122 is illustrated having on one side a scene 124, such as a child pulling a training pant up, while the opposite side of the card 122 can include a definition or written description 126 of scene 124.

FIG. 11 illustrates an activity device 62 such as stickers 130 that are releasably adhered to a release paper 128. The stickers 130 can be removed and placed wherever appropriate, such as on progress chart 68 (FIG. 6).

These items illustrated in FIGS. 10 and 11 are representative of the types of devices 56, 62 that can be used by the mother and child during the toilet training process. As explained earlier, it is important to a child's successful progression through the toilet training process to have proper encouragement and motivation provided by his or her caregivers, and to have a sense of ownership and independence. Additionally, the ease of portability of kit 10, and the fact that kit 10 is self-contained, further encourage and motivate the child to progress successfully and quickly through the toilet training process.

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed is:

1. A self-contained, interactive toilet training kit, comprising:

a case including a bottom wall, a continuous side wall forming with said bottom wall an interior and an opening, and a lid comprising an inner surface and being moveable between a closed position that covers said opening and an open position that exposes said opening, an interactivity device for instructing a child in toilet training, an activity device for use by the child in toilet training, a partition forming at least two compartments in said interior, one of said compartments containing at least one training pant, and the other of said compartments containing at least one of said activity device and said interactivity device, and a learning graphic on said inner surface of said lid for instructing a child in toilet training.

2. The kit of claim 1 wherein said lid is hingedly connected to said continuous side wall, and said case further includes a locking means for releasably locking said lid in said closed position.

3. The kit of claim 1 wherein said continuous side wall comprises at least three planar walls.

4. The kit of claim 1 wherein said continuous side wall is arcuate.

5. The kit of claim 1 wherein said case further includes a carrying handle.

6. A self-contained, interactive toilet training kit, comprising:
 a case having an interior, and including a bottom wall, a continuous side wall, an outer surface, an inner surface, and a lid having a top surface and an inner surface and being moveable between a closed position and an open position,
 at least one partition in said interior dividing said interior into at least two compartments,
 a plurality of training pants in one of said compartments,
 at least one activity device in the other of said compartments, and
 an interactivity device on said outer surface of said case for instructing a child in toilet training.

7. The kit of claim 6 wherein said case further includes a carrying handle.

8. The kit of claim 7 wherein said case further includes a locking means for releasably locking said lid in said closed position.

9. The kit of claim 8 wherein said lid is hingedly connected to said continuous side wall.

10. The kit of claim 6 further including one of said activity device and said interactivity device on said top surface of said lid.

11. The kit of claim 10 further including one of said activity device and said interactivity device on said inner surface on said lid.

* * * * *